United States Patent [19]
Welch et al.

[11] Patent Number: 5,667,499
[45] Date of Patent: Sep. 16, 1997

[54] GUIDE CATHETER UNIBODY

[75] Inventors: Jeffrey M. Welch, New Hope; Todd A. Berg, Lino Lakes; Thomas J. Bachinski, Lakeville; Kevin M. Klitz, Plymouth, all of Minn.

[73] Assignee: SciMed Life Systems, Inc., Maple Grove, Minn.

[21] Appl. No.: 317,724

[22] Filed: Oct. 4, 1994

[51] Int. Cl.$^6$ ................................................ A61M 25/00
[52] U.S. Cl. ..................... 604/282; 604/280; 128/658; 138/125
[58] Field of Search ..................... 604/264, 280, 604/282; 128/772, 656–658; 138/123, 124, 125, 132–134, 137, 141, 142, 143–146

[56] References Cited

U.S. PATENT DOCUMENTS

| | | | |
|---|---|---|---|
| 419,926 | 1/1890 | Chapman . | |
| 2,472,483 | 6/1949 | Krippendorf | 132/49 |
| 3,416,531 | 12/1968 | Edwards | 128/348 |
| 3,485,234 | 12/1969 | Stevens | 128/2 |
| 3,924,632 | 12/1975 | Cook | 128/348 |
| 3,965,909 | 6/1976 | Waddell et al. | 128/348 |
| 4,100,309 | 7/1978 | Micklus et al. . | |
| 4,321,226 | 3/1982 | Markling | 264/139 |
| 4,425,919 | 1/1984 | Alston, Jr. et al. | 604/282 X |
| 4,516,972 | 5/1985 | Samson | 604/282 |
| 4,547,193 | 10/1985 | Rydell | 604/282 |
| 4,563,181 | 1/1986 | Wijayarathna et al. | 604/280 |
| 4,577,543 | 3/1986 | Wilson | 604/282 X |
| 4,596,563 | 6/1986 | Pande | 604/246 |
| 4,636,346 | 1/1987 | Gold et al. | 264/139 |
| 4,655,771 | 4/1987 | Wallsten | 604/282 X |
| 4,665,604 | 5/1987 | Dubowik | 29/415 |
| 4,737,153 | 4/1988 | Shimamura et al. | 604/282 |
| 4,817,613 | 4/1989 | Jaraczewski et al. | 128/658 |
| 4,842,590 | 6/1989 | Tanabe et al. | 604/282 |
| 4,863,442 | 9/1989 | DeMello et al. | 604/282 |
| 4,898,591 | 2/1990 | Jang et al. | 604/282 |
| 4,904,431 | 2/1990 | O'Maleki | 264/143 |
| 4,907,624 | 3/1990 | Jonasson . | |
| 4,923,061 | 5/1990 | Trombley, III . | |
| 4,935,017 | 6/1990 | Sylvanowicz | 604/280 |
| 4,994,047 | 2/1991 | Walker et al. | 604/264 |
| 5,019,057 | 5/1991 | Truckai | 604/282 |
| 5,045,072 | 9/1991 | Castillo et al. | 604/280 |
| 5,057,092 | 10/1991 | Webster, Jr. | 604/282 |
| 5,061,257 | 10/1991 | Martinez et al. | 604/282 |
| 5,069,674 | 12/1991 | Fearnot et al. | 604/282 |
| 5,078,702 | 1/1992 | Pomeranz | 604/280 |
| 5,163,431 | 11/1992 | Griep . | |
| 5,171,232 | 12/1992 | Castillo et al. | 604/280 |
| 5,176,660 | 1/1993 | Truckai | 604/282 |
| 5,221,270 | 6/1993 | Parker | 604/282 |
| 5,222,949 | 6/1993 | Kaldany | 604/282 |
| 5,234,416 | 8/1993 | Macaulay | 604/282 |
| 5,248,305 | 9/1993 | Zdrahala | 604/280 |
| 5,254,107 | 10/1993 | Soltesz | 604/282 |
| 5,267,982 | 12/1993 | Sylvanowicz | 604/281 |
| 5,279,596 | 1/1994 | Castaneda et al. | 604/282 |
| 5,290,229 | 3/1994 | Paskar | 604/95 |
| 5,290,230 | 3/1994 | Ainsworth et al. | 604/96 |
| 5,306,263 | 4/1994 | Voda | 604/281 |
| 5,318,032 | 6/1994 | Lonsbury et al. . | |
| 5,322,509 | 6/1994 | Rickerd | 604/53 |
| 5,334,168 | 8/1994 | Hemmer | 604/281 |
| 5,334,169 | 8/1994 | Brown et al. | 604/282 |
| 5,335,410 | 8/1994 | Burnham | 29/452 |
| 5,383,923 | 1/1995 | Webster, Jr. | 607/125 |
| 5,389,090 | 2/1995 | Fischell et al. | 604/280 |
| 5,423,773 | 6/1995 | Jimenez | 604/283 |

*Primary Examiner*—Corrine M. McDermott
*Assistant Examiner*—Ronald K. Stright, Jr.
*Attorney, Agent, or Firm*—Nawrocki, Rooney & Sivertson, P.A.

[57] ABSTRACT

Guide catheter unibody and method for manufacturing such a catheter. In one preferred embodiment, the present invention is a unibody guide catheter for use in percutaneous transluminal angioplasty procedures. The catheter includes a base layer and a structural layer formed over the base layer. The structural layer includes strands which cross at a plurality of points, the strands being attached together for structural integrity at a substantial number of points where they cross. The structural layer may be at least partially embedded in the base layer. Additionally, a cover layer is formed over the structural layer.

30 Claims, 7 Drawing Sheets

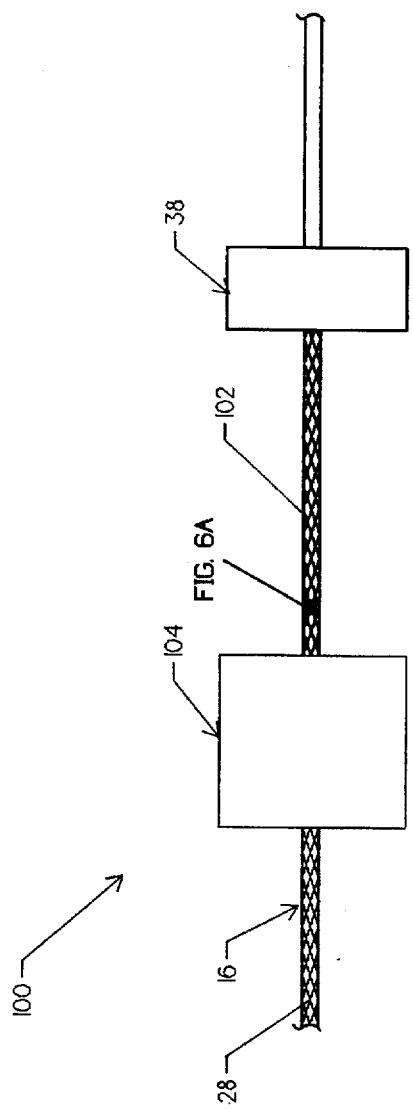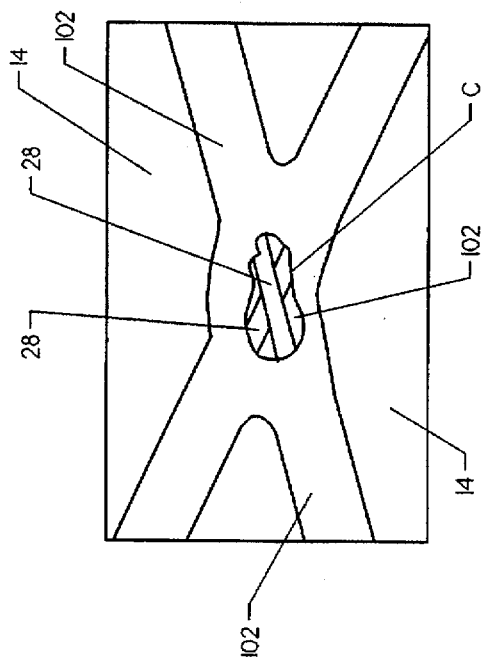

GUIDE CATHETER UNIBODY

BACKGROUND OF THE INVENTION

1. Field of the Invention

The present invention relates to guide catheters and method of manufacturing guide catheters. In particular, the present invention relates to an improved guide catheter unibody which resists kinking and provides better torque control.

2. Description of the Prior Art

Percutaneous transluminal angioplasty is widely accepted as an efficient and effective method for treating various obstructive disorders and vascular diseases. In particular, angioplasty is widely used for opening stenosis in coronary arteries, although it is also used for treatment of stenosis in other parts of the vascular system.

Guide catheters are well known for use in angioplasty procedures. In a typical angioplasty procedure, the guide catheter is initially inserted into an artery, such as the femoral artery or axial artery. Subsequently, the catheter is advanced transluminally to a point where the distal tip of the guide catheter is positioned within a blood vessel, near the obstructive lesion or stenosis to be treated. Alternatively, the guide catheter may be inserted preloaded, and contain a dilatation balloon and guide wire when it is initially inserted.

Next, a flexible guide wire is inserted through the lumen of the guide catheter with the distal end of the guide wire extending beyond the distal tip of the guide catheter. The guide wire is advanced, while monitored using fluoroscopy, to a point where the distal end of the guide wire is advanced past the arterial obstruction or stenosis. A dilatation balloon catheter is then inserted and advanced over the guide wire through the lumen of the guide catheter to a point where the balloon of the dilatation balloon catheter is positioned across the stenosis. The balloon is then inflated by supplying a fluid under pressure through an inflation lumen to the balloon. The balloon is inflated and deflated, pressing the lesion into the artery wall to reestablish acceptable blood flow through the artery. Upon completion of the balloon dilatation procedure, the deflated dilatation balloon catheter and guide wire are withdrawn from the patient's body using the guide catheter lumen. Lastly, the guide catheter itself is removed from the patient's body.

In angioplasty procedures, the guide catheter must be able to traverse tortuous pathways through blood vessels to the stenosis, in a manner atraumatic as possible. Therefore, to limit insertion time and discomfort to the patient, the guide catheter must be stiff enough to resist the formation of kinks, while at the same time possess flexibility to be responsive to maneuvering forces when guiding the catheter through the vascular system. It is important that the guide catheter exhibit good torque control such that manipulation of a proximal portion of the guide catheter is responsively translated to the tip or distal end of the catheter to curve and guide the guide catheter through the tortuous pathways.

In an attempt to meet the above guide catheter performance requirements, various guide catheter construction methods are used. U.S. Pat. No. 4,665,604 to Dubowik suggests a guide catheter which includes a base strand, a braided layer, and a final layer. First, the base strand is formed by extruding a material onto a wire mandril. Next, stainless steel wire is braided over the base strand to form the braided layer. Sections of the braid which will form the body of the catheter are imbedded in the base strand by re-passing the base strand through a heated dye. Lastly, the final coating is extruded over the braided layer.

Similarly, U.S. Pat. No. 4,321,226 to Markling suggests a method of catheter body construction which includes a first plastic layer extruded on a core wire, a wire braid applied onto the first plastic layer, and finally, a second plastic layer extruded over the wire braid. The wire braid is formed of cross-wound individual stainless steel wires.

U.S. Pat. No. 4,577,543 to Wilson suggests another similar method of catheter body construction which includes a generally cylindrical body having reinforcement material braided over the body. The body, with reinforcing strands, passes through a heated dye so that the braided strands adhere to the surface of the body. Wilson suggests that the strands may be of reinforcing material such as metal wire (steel wire) or synthetic fibers (fiberglass or aramid).

The above types of catheter construction still tend to form kinks when traversing tortuous blood vessel pathways. The braided layer lacks a tight fitting braid and evenness of joinder at the points where the wires cross in the braid. This problem results in lack of good torque control necessary for manipulation of a proximal portion of the guide catheter to impart forces at the catheter's distal end needed to curve and guide the catheter through the blood vessels.

Other guide catheter construction methods are used, which do not have a braided reinforcing layer. Such a method is suggested in U.S. Pat. No. 4,596,563 to Pande, which includes a method for making a tubular catheter having two layers. The two layers are formed of polymeric material and include a rigid inner sheath and a flexible outer sheath. The rigid inner sheath is extruded onto a mandril, and the flexible outer sheath is extruded over the rigid inner sheath. Similarly, U.S. Pat. No. 4,636,346 to Gold et al. suggests the preparation of a guide catheter having a three-layered tubular body which includes an inner sheath, a rigid intermediate sheath, and a flexible outer sheath. The rigid intermediate sheath is formed from extruding polymeric materials such as polycarbonates and polyamides over the interior sheath. Such catheters lack the structural integrity and torque response provided by a reinforcing braided layer for maneuvering the catheter through tortuous pathways of a patient's vascular system.

SUMMARY OF THE INVENTION

The present invention is a unibody guide catheter for use in percutaneous transluminal angioplasty procedures and a method of manufacturing such a catheter. The catheter includes a base layer and a structural layer formed over the base layer. The structural layer includes a plurality of strands which cross at a plurality of points. The strands are attached to each other at a substantial number of points where they cross. Additionally, a cover layer is formed over the structural layer.

In another embodiment, the present invention includes a torque control guide catheter having a unibody. The unibody includes a tubular base member, a reinforcement member and a flexible cover. The tubular base member is formed from extruded plastic and has a lubricous inner surface. The reinforcement member includes strands which are bonded together and may be at least partially embedded in the tubular base member. The flexible cover is extruded over the tubular base member.

In another embodiment, the present invention includes a unibody guide catheter for use in percutaneous transluminal angioplasty procedures, having a multilayered unibody. The unibody includes a flexible tubular base member, a reinforcement layer, and a cover layer. The reinforcement layer includes a plurality of strands which are braided onto the tubular base member. The strands are attached to each other at a substantial number of points where they cross. Additionally, the cover layer is formed over the structural layer.

In one embodiment, the strands include a core wire having a coating. The core may be formed of any metal wire, such as a stainless steel wire. The coating is formed from a suitable polymeric material, such as a thermoplastic polymer. The strands are attached to each other at a substantial number of points in the braid where they cross by passing the tubular member having a braided reinforcement layer through a heated dye which bonds the thermoplastic polymer coating of the strands together at the points where they cross. For further structural integrity, the braided reinforcement layer may be at least partially embedded in the tubular base member.

In one preferred embodiment, the coating is formed from Nylon, which is a trademark of DuPont. Alternatively, the coating may be formed of other suitable material. For example, it is recognized that the coating may be formed from polyether block amide (PEBA) or a Nylon-PEBA blend.

Alternatively, the strands may have a nonmetallic core. For example, the strand cores may be formed from a hard polyamide, such as a Kevlar, or Liquid Crystal Polymer (LCP).

The present invention includes a method for preparing a guide catheter used in percutaneous transluminal angioplasty procedures, the method includes a plurality of steps. The first step includes forming a tubular base layer around a mandrel. Next, a structural layer is formed over the base layer. The structural layer includes a plurality of strands, wherein the strands cross at a plurality of points. Next, the structural layer strands are attached together. For additional structural integrity, the structural layer may be at least partially embedded in the base layer. Finally, the mandrel is removed resulting in a tubular guide catheter.

The structural layer strands may be formed over the base layer by known methods, such as braiding or helical wrapping. The strands include a core wire, such as stainless steel, which has a cover layer. The cover layer is formed of a different material. In one embodiment, the cover layer is a polymeric material, such as nylon.

The structural layer strands may be attached together by many methods. In one embodiment the strands are attached together by passing the guide catheter through a heated dye which bonds the thermoplastic polymer coatings of the strands together at a substantial number of points where they cross. It is recognized that many known methods of thermal heating may be used to bond the strand coatings together at the points where they cross.

In another embodiment, the strands include a core having a thermoset polymer coating. The strands are attached together by passing the guide catheter through a heated dye. The strands are chemically bonded together at a substantial number of points where they cross. Upon reheating, the strands remain chemically bonded together at a substantial number of points where they cross.

Alternatively, an electrical current may be passed through the wire braid, heating the wire braid and attaching the strands together at the point where they cross. Other methods may be used, such as spot welding the strands together at a substantial number of points where they cross, or through the use of laser welding methods.

In another embodiment, the present invention includes a unibody catheter having a base layer and a structural layer formed over the base layer. The structural layer includes a plurality of strands, wherein the strands cross at a plurality of points. The strands are attached together at a substantial number of points where they cross by a metallurgical connection.

The strands are attached together by forming a metallic substrate over the strands. The metallic substrate may be formed of metal, such as nickel, or a metal blend. A mechanism is provided for varying the thickness of the metallic substrate. In one embodiment, the metallic substrate is formed on the structural layer strands by an electrochemical process, such as an electrolytic bath.

By forming a metallic substrate over the catheter structural layer, the strands are attached together at a substantial number of points where they cross by a metallurgical connection. The metallic substrate provides a more rigid connection with a higher tensile strength, resulting in a more responsive catheter.

After the structural layer strands are attached together, the braided strands may be at least partially embedded in the base layer for additional structural integrity. Alternatively, the braided structural layer may be first at least partially embedded in the base layer, and then the braided structural layer strands may be attached together. Finally, the cover layer is formed over the structural layer.

Attaching the strands of the structural layer to each other at a substantial number of points where they cross improves the structural integrity and improves angioplasty procedure performance response of the guide catheter. The improved guide catheter is less likely to kink when being guided through a patient's tortuous vascular system, leading to more successful angioplasty procedures. Additionally, the physical looseness in the braids of the structural layer is reduced due to the fixed attachments of the strands at the points in the braid where they cross. This results in better catheter performance due to a better transmission of torque from manipulation forces at a proximal end of the catheter to the distal end of the catheter for guiding the catheter through tortuous blood vessels.

BRIEF DESCRIPTION OF THE DRAWINGS

The invention will be further described with reference to the accompanying drawings where like numbers refer to like parts in several views and wherein:

FIG. 6 is a partial schematic view illustrating a method of manufacturing another embodiment of a guide catheter according to the present invention;

FIG. 6A is an expanded partial side view of the guide catheter of FIG. 6 showing the metallic substrate;

DETAILED DESCRIPTION OF THE PREFERRED EMBODIMENTS

Figure 1:
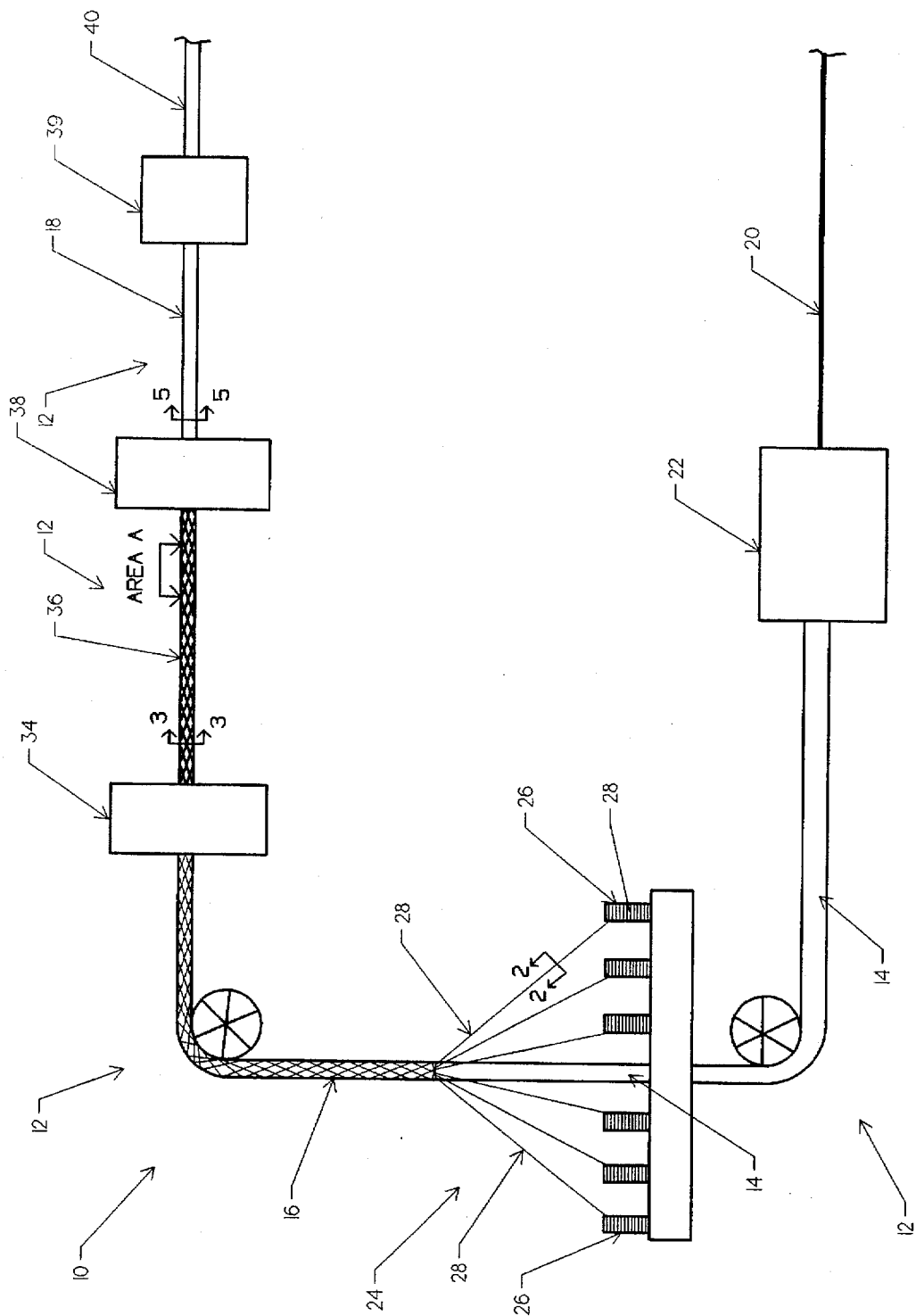
FIG. 1 is a schematic view illustrating a method of manufacturing a guide catheter according to the present invention.

FIG. 1 shows a schematic view of a guide catheter method of construction at 10, for manufacturing a guide catheter 12. Guide catheter 12 is multi-layered within a single unibody, and includes a base layer 14, a structural layer 16 and a coating 18.

As shown in FIG. 1, base layer 14 is formed by passing a mandril 20 through a first extruder 22. First extruder 22 extrudes a suitable plastic onto mandril 20 using a commonly known conventional extrusion process. In one embodiment, mandril 20 is formed of silver-coated copper wire, and base layer 14 is formed of a thin coat of semi-soft plastic elastomeric material having a lubricous inner surface. In one preferred embodiment, the base layer 14 is formed from polytetrafluoroethylene (PTFE). First extruder 22 extrudes a thin base layer 14 onto mandril 20. Mandril 20 forms base layer 14 in a tubular shape, and is sized such that later removal of the mandril 20 will provide guide catheter 12 with a lumen sized to carry various intravascular catheter devices.

Figure 2:
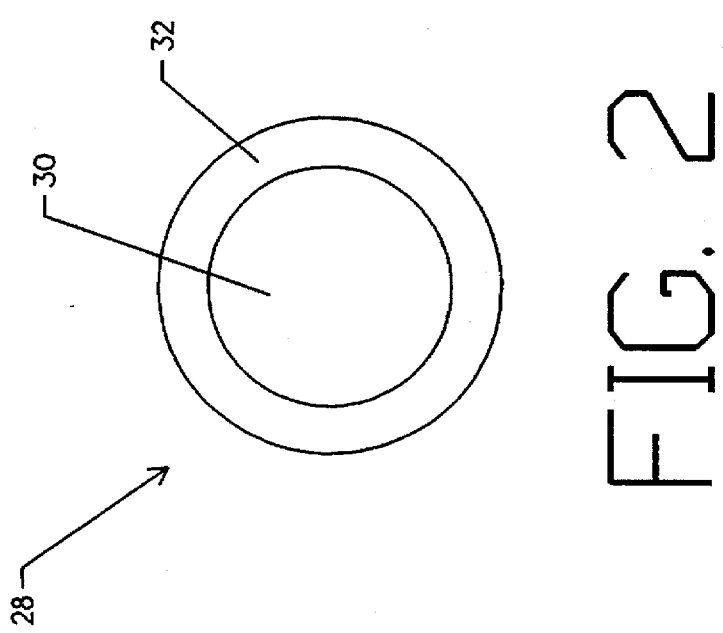
FIG. 2 is a cross-sectional view of a braid strand taken along line 2—2 of FIG. 1.

Next, guide catheter 12 is cooled and run through a braiding machine 24 for braiding structural layer 16 on base layer 14. Braiding machine 24 includes spools 26 having strands 28. FIG. 2 is a sectional view of strand 28 taken along line 2—2 of FIG. 1. Strand 28 includes a core 30 having a thermoplastic polymer coating 32. In a preferred embodiment, core 30 consists of stainless steel wire, and coating 32 is a thermoplastic polymer coating, such as Nylon, approximately 0.001 inches thick.

As catheter 12 is run through braiding machine 24, strands 28 are tightly braided onto base layer 14 to form structural layer 16. Braiding machine 24 includes sixteen spools 26 (six shown). Braiding machine 24 tightly wraps strands 28 from spools 26 over base layer 14 in a braided pattern at, for example, a forty per inch crossings (PIC) count, to form structural layer 16. It is recognized that braiding machine 24 may be a conventional wrapping device which wraps strands around a tubular body by braiding or helical wrapping.

Next, guide catheter 12, having structural layer 16, is passed through a heated dye 34. Heated dye 34 performs two main functions. Heated dye 34 functions to embed structural layer 16 in base layer 14. Also, heated dye 34 functions to improve the structural integrity of guide catheter 12 by bonding together the braided strands of structural layer 16.

Figure 3:
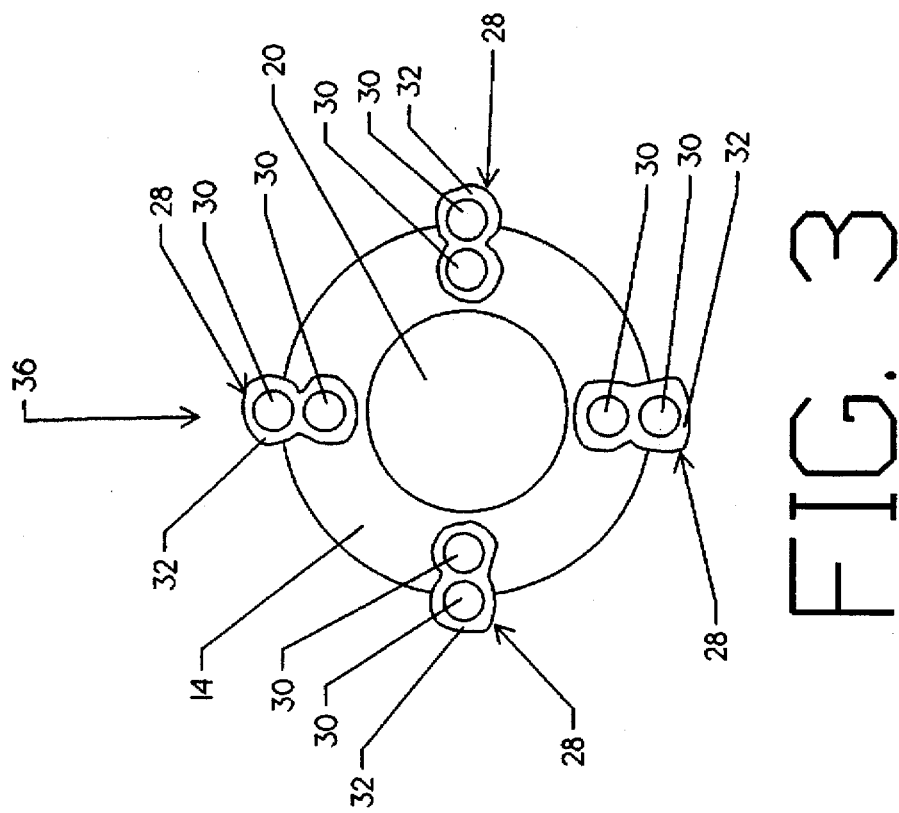
FIG. 3 is a cross-sectional view of the guide catheter taken along line 3—3 of FIG. 1.

As catheter 12 passes through heated dye 34, structural layer 16 is embedded in base layer 14, as shown in FIG. 3. Structural layer 16 may be fully embedded or partially embedded in base layer 14, or alternatively, may remain flush with the base layer 14 surface. As known in the art, selected sections of structural layer 16 may be left unembedded in base layer 14 and later removed by a mechanical or electrical process to form the tip for a non-fused catheter.

As previously stated, heated dye 34 also performs an important function of bonding braided strands 28 together at the points where they cross. Bonded structural layer is indicated at 36. FIG. 3 shows a cross section along line 3—3 of FIG. 1 of bonded structural layer 36 at a point where braided strands 28 cross. As shown in FIG. 3, strands 28 are partially embedded in base layer 14. After passing through heated dye 34, strands 28 are bonded or fused together at the locations where they cross. The bonding of braided strands 28 adds structural integrity to structural layer 16 and the finished guide catheter 12.

Before braided strands 28 pass through heated dye 34, braided strands 28 overlap at the locations where they cross. The overlapping of braided strands 28 results in loose crossings in guide catheter 12 and results in a physically loose structural layer 16. It is necessary for a guide catheter to maintain a certain degree of stiffness to avoid kinking problems. Lack of structural integrity from the loose guide catheter braid leads to kinking of the guide catheter during an angioplasty procedure. When kinking occurs, the time required for successful insertion of the catheter greatly increases, thereby decreasing the patient's chance of a successful angioplasty procedure. Additionally, catheter performance is decreased from the lack of structural integrity due to torque forces being inefficiently transmitted from manipulation of a proximal end of the catheter to a distal end of the catheter for guiding the catheter through a patient's tortuous vascular system.

Figure 4:
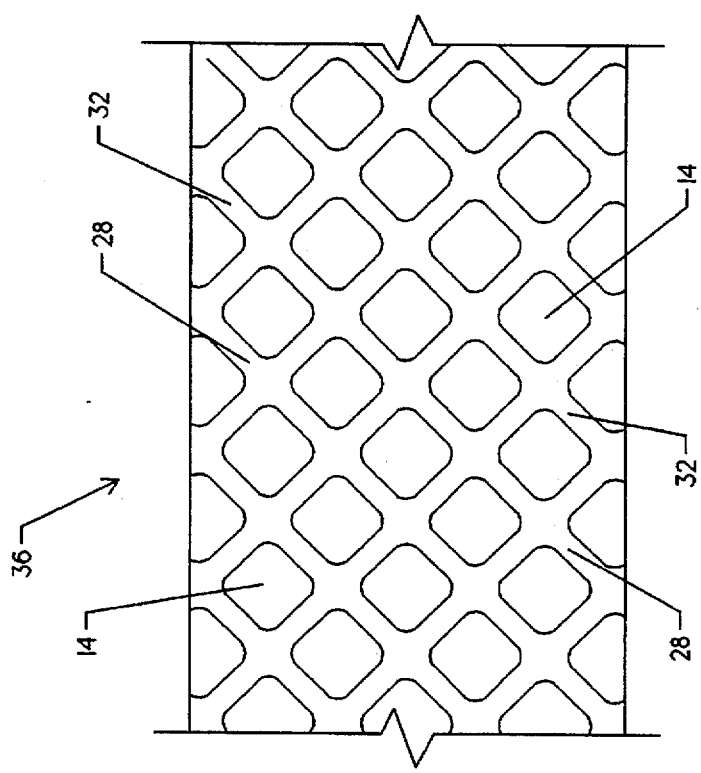
FIG. 4 is a side view of the guide catheter taken at Area A of FIG. 1.

FIG. 4 shows a side view of catheter 12 bonded structural layer 36 at area A in FIG. 1. After passing through heated dye 34, braided strands 28 are coupled together at the locations 34, where they cross. Heated dye 34 bonds or fuses the coating 32 of strands 28 together, resulting in evenness of joinder and the braided strands 28 being fixedly secured together at their joints. All the strands 28 may be bonded together at the point where they cross, or they may be attached to each other at a substantial number of points where they cross.

Coupled strands 28 improve the structural integrity and improve angioplasty procedure performance response of guide catheter 12. With bonded structural layer 36, guide catheter 12 is less likely to kink when being guided through a patient's tortuous vascular system, leading to more successful angioplasty procedures. Additionally, the physical looseness in the braids is gone due to the fixed attachments of the strands at the points in the braids where they cross, resulting in better catheter performance due to a better transmission of torque from manipulation forces at a proximal end of the catheter to the distal end of the catheter for guiding the catheter through tortuous blood vessels.

It is recognized that other methods may be used for attaching the braided strands to each other at the points where they cross. For example, the braided strands may be attached together bypassing an electrical current through the braided structural layer. Alternatively, the braided strands may be spot welded or laser welded at the points where they cross for fusing or bonding the strands together. The braided strands may be attached together while also bonding to the guide catheter base layer. Similar methods may be used which will not deviate from the scope of this invention.

Additionally, it is recognized that other methods be used to provide more support to the structural layer by joining the strands so they are not able to move relative to each other. For example, the structural layer may be woven, or alteratively, knots may be formed by the strands in at least a substantial number of points where they cross.

In one embodiment, the strands include a core having a thermoset polymer coating. The strands are attached together by passing the guide catheter through a heated dye. Alternatively, the strands may be attached together by other methods which provide a cross link reaction such as other heating methods, exposure to a light source such as UV light, or by chemical means. The strands are chemically bonded together at a substantial number of points where they cross. Upon reheating, the strands remain chemically bonded together at a substantial number of points where they cross.

Alternatively, the strands may have a nonmetallic core. For example, the strand cores may be formed from a hard polyamide, such as Kevlar, or Liquid Crystal Polymer (LCP).

Figure 5:
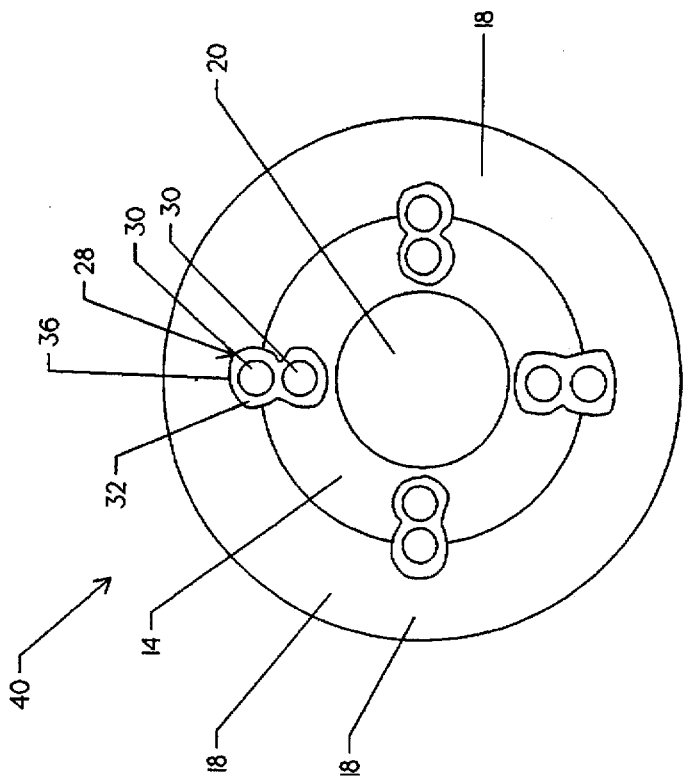
FIG. 5 is a cross-sectional view of the guide catheter taken along line 5—5 of FIG. 1.

After passing through heated dye 34, guide catheter 12 is cooled. Next, guide catheter 12 passes through a second extruder 38 forming a smooth coating 18 over bonded structural layer 36. Coating 18 consists of commonly used catheter cover material, such as a PEBA blend or an elastomeric polyurethane. FIG. 5 is a sectional view of guide catheter 12 taken along line 5—5 of FIG. 1, showing coating 18 extruded over bonded structural layer 36.

Lastly, mandril 20 is removed from guide catheter 12, indicated at 39, resulting in a finished guide catheter unibody 40. Guide catheter unibody 40 has improved performance characteristics for angioplasty procedures, due to the added structural integrity of the bonded structural layer which limits kinking and greatly improves torque performance. Guide catheter unibody 40 maintains high flexibility having a lubricious tubular inner surface formed from soft extruded plastic or PEBA for passing angioplasty devices through the catheter lumen, and further including a thin, smooth cover layer for passing the guide catheter unibody through a patient's tortuous vascular system.

In yet another embodiment shown generally at 100 in FIG. 6, after strands 28 are braided onto base layer 14, forming structural layer 16, a metallic substrate 102 is placed over the braided strands 28. The metallic substrate 102 may consist of nickel or other metallic substances or metallic blend of materials. The metallic substrate is plated onto braided strands 28 by substrate process 104. Substrate process 104 may be a process, such as plating, extrusion, or other continuous coating processes. The metallic substrate 102 bonds or fuses the strands 28 together, resulting in the strands 28 being fixedly secured together at a substantial number of points where they cross.

FIG. 6A is an expanded partial view of the guide catheter of FIG. 6 showing the metallic substrate 102. FIG. 6A includes a cutaway C showing strands 28 at a point where they cross. Metallic substrate 102 is plated around strands 28, securely attaching strands 28 together at the points where they cross.

Figure 7:
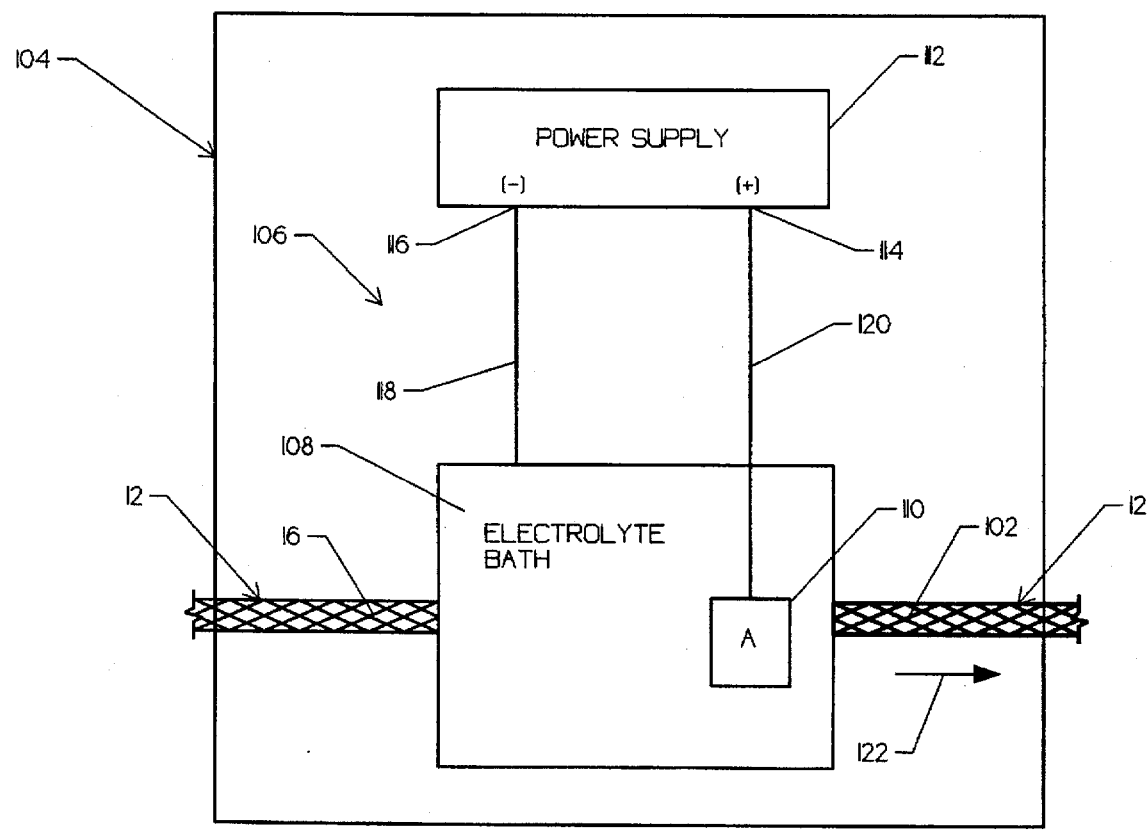
FIG. 7 is a schematic view of the substrate process of FIG. 6.

In one embodiment, the substrate process 104 is an electrochemical process as shown generally at 106 in FIG. 7. The electrochemical process 106 includes an electrolyte bath 108, metal anode 110, and power supply 112 having a positive terminal 114 and a negative terminal 116. Guide catheter 12, having braided structural layer 16, is routed through electrolyte bath 108 for plating a metallic substrate 102 on guide catheter 12.

Electrolyte bath 108 includes a solution of nickel chloride, hydrochloric acid, and deionized water. Anode 110 is located within electrolyte bath 108. Anode 110 is formed of metal, such as nickel, tin, or copper, or a combination of metals. In one preferred embodiment, anode 110 is 99.9% pure nickel.

Power supply 112 provides a positive and negative charge to electrochemical process 106. Negative terminal 116 is electrically coupled to guide catheter 12 structural layer 16, indicated at 118. Positive terminal 114 is electrically coupled to anode 110, indicated at 120. The amount of power supplied by power supply 112 to the electrochemical process 106 may be variable, or alternatively, may be constant.

In operation, guide catheter 12 is moved through electrolyte bath 108 at a desired rate as indicated by directional arrow 122. Power supply 112 provides a positive charge to anode 110 and a negative charge to the guide catheter structural layer 16. As the guide catheter 12 passes through electrolyte bath 108, nickel atoms flow from the positive charged anode 110 to the negative charged braided structural layer 116 and attach themselves to the braided strands 28. This electrochemical process 106 results in a metallic substrate 102 plated on structural layer 116.

The degree of metallic substrate plating 102 on structural layer 16 may be varied by varying the amount of power supplied by power supply 112. Increasing the power to electrolyte bath 108, increases the flow of nickel atoms from anode 110 to structural layer 16. Additionally, the amount of metallic substance 102 plated on guide catheter 12 may be varied by varying the rate at which guide catheter 12 passes through electrolyte bath 108. A slower rate results in an increased metallic substrate 102.

The electrochemical process 106 attaches the structural layer 16 braids to each other at a substantial number of points where they cross. Plating a metal, such as nickel, onto structural layer 16 provides a metallurgical connection between the structural braids at a substantial number of points where they cross. The metallurgical connection is a rigid connection, providing increased tensile strength over less rigid non-metals. Plating metals, such as nickel, are tough, ductile, and easy to plate. Plating metallic substrate 102 on guide catheter 12 results in a more responsive guide catheter 12.

Figure 8:
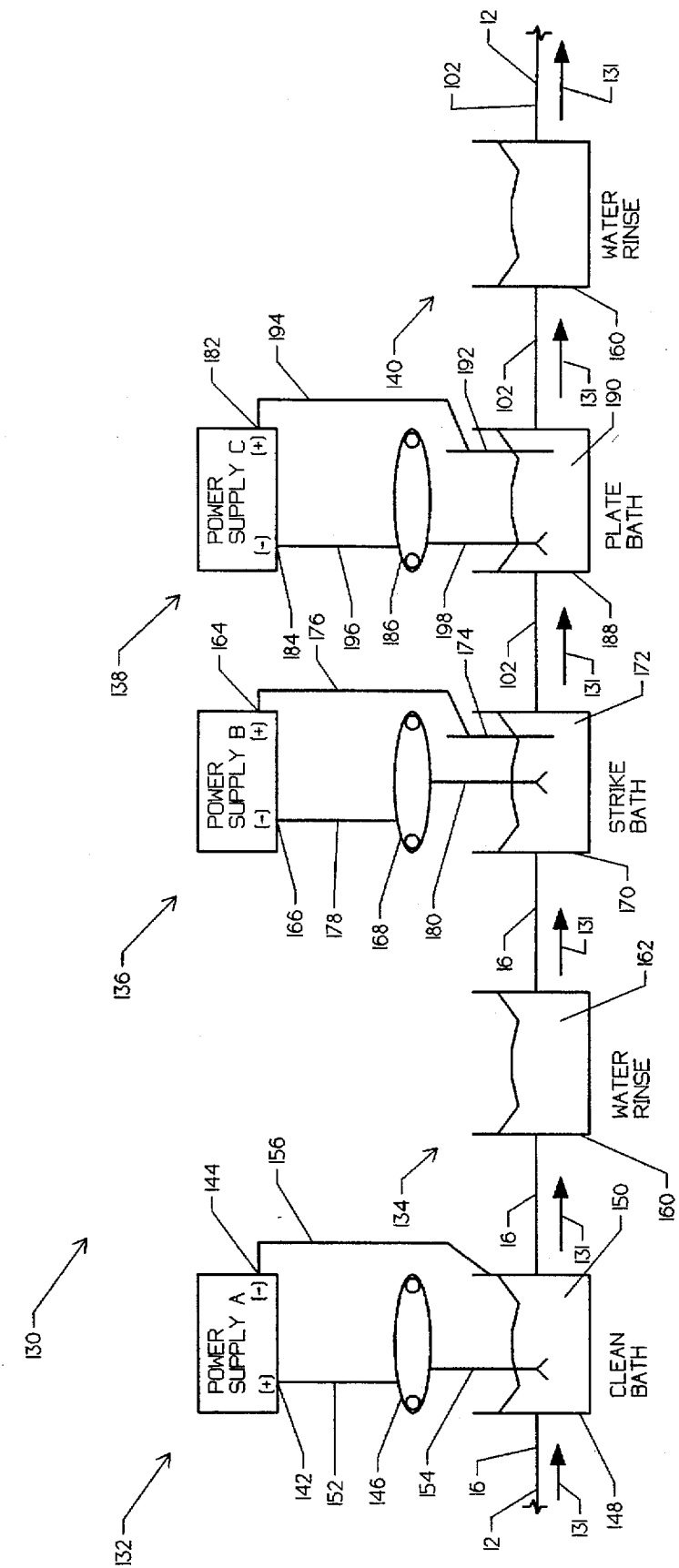
FIG. 8 is a schematic view of an alternative embodiment of the substrate process of FIG. 6.

Yet another preferred process for plating a metallic substrate 102 over guide catheter 12 structural layer 16 is shown in schematic form in FIG. 8, generally at 130. Electrochemical process 130 includes clean bath 132, water rinse 134, strike bath 136, plate bath 138, and water rinse 140. Guide catheter 12 moves through electrochemical process 130 at a desired rate, as indicated by directional arrows 131. As guide catheter 12 moves through the electrochemical process 130, a metallic substrate 102 is plated onto the guide catheter structural layer 16 for attaching the structural layer 16 braids together at a substantial number of points where they cross.

Clean bath 132 includes power supply A having positive terminal 142 and negative terminal 144, moveable track 146, clean bath enclosure 148, and clean bath solution 150. Positive terminal 142 is electrically coupled to track 146, indicated at 152. Track 146 is electrically coupled to the guide catheter 12 structural layer 16 braids, indicated at 154. Track 146 is moveable and provides a continuous electrical connection between positive terminal 142 and guide catheter 12 structural layer 16 while guide catheter 12 moves through clean bath 132.

Negative terminal 144 is electrically coupled to clean bath enclosure 148, indicated at 156. Clean bath solution 150, contained within enclosure 148, is an electrochemical cleaning solution mixture which includes a mixture of sodium hydroxide and water. The electrochemical cleaning solution 150 electrically scrubs the surface of guide catheter 12 as guide catheter 12 moves through the clean bath 132. Power supply A provides a positive charge on structural layer 16 and a negative charge on clean bath enclosure 148. In operation, as guide catheter 12 moves through the clean bath solution 150, unwanted materials flow from the positively charged guide catheter structural layer 16 to the negatively charged clean bath enclosure 148.

Water rinse 134 includes enclosure 160 which contains deionized water 162. Guide catheter 12 moves through enclosure 160 and deionized water 162 for rinsing unwanted particles from guide catheter 12. Water rinse 134 contains cleaned and filtered water that rinses away contaminants which may effect the electrical conductivity of structural layer 16.

Strike bath 136 includes power supply B having a positive terminal 164 and negative terminal 166, track 168, enclosure 170, strike bath solution 172, and anode 174. As guide catheter 12 moves through strike bath 136, strike bath 136 operates to provide a thin layer of metal substrate 102 on structural layer 16. The thin layer of metallic substrate 102 operates as an introducer, providing for adherence of a greater mass of metallic substrate 102 in the plate bath 138.

In strike bath 136, power supply B positive terminal 164 is electrically coupled to anode 174, indicated at 176. Negative terminal 166 is electrically coupled to moveable track 168 indicated at 178. Moveable track 168 is electrically coupled to guide catheter structural layer 16 indicated at 180. Moveable track 168 allows a negative charge to be induced on structural layer 16 while guide catheter 12 moves through the strike bath solution 172.

Anode 174 is formed of a metal or a mixture of metals, such as nickel, tin, stainless steel, or copper. In a preferred embodiment, anode 174 is formed of 99.95% pure nickel. Guide catheter 12 moves at a continuous rate through strike bath solution 172. In one embodiment, strike bath solution 172, contained within enclosure 188, is a nickel chloride solution which includes hydrochloric acid and deionized water.

As guide catheter 12 moves through strike bath solution 172, positively charged nickel atoms are attracted to and flow to the negatively charged structural layer 16 braid. The nickel atoms attach themselves to the structural layer 16 braided strands, forming a thin layered metallic substrate 102 around structural layer 16. The thin metallic substrate 102 formed of nickel on structural layer 16 allows for adherence of a greater mass of nickel to be plated on structural layer 16 in the next plate bath 138.

Plate bath 138 includes a power supply C having a positive terminal 182, a negative terminal 184, a moveable track 186, an enclosure 188, a plate bath solution 190, and an anode 192. Plate bath 138 plates a greater mass of nickel over guide catheter 12 than strike bath 136, to form metallic substrate 102.

Power supply C positive terminal 182 is electrically coupled to anode 192 at 194. Power supply C negative terminal 184 is electrically coupled to moveable track 186 at 196. Moveable track 186 is electrically coupled to guide catheter 12 structural layer 16 at 198. Moveable track 186 allows for a continuous electrical connection between negative terminal 184 and structural layer 16 as guide catheter 12 moves through plate bath solution 190.

Similar to strike bath 136, anode 192 is formed of a metallic substance, such as nickel. In a preferred embodiment, anode 192 is formed of 99.95% pure nickel. Also, plate bath solution 190, contained within enclosure 188, may be a solution which includes a mixture of nickel chloride, nickel sulfamate, boric acid, and deionized water.

As guide catheter 12 moves through plate bath 138, nickel atoms flow from the positively charged anode 192 to the negatively charged structural layer 16. By increasing the power supplied by power supply C and resulting current to structural layer 16, a greater amount of nickel flows from anode 192 to structural layer 16 in the plate bath 138.

After leaving plate bath 138, guide catheter 12 moves through water rinse 140. Like water rinse 134, water rinse 140 includes an enclosure 160 containing deionized water 162. The water rinses unwanted material from metallic substrate 102 formed over structural layer 16.

Power supplies B and C are variable power supplies. By increasing the amount of power supplied to strike bath 136 and plate bath 138, the amount of nickel plated on structural layer 16 is increased.

Guide catheter 12 moves through electrochemical process 130 at a constant rate. In one embodiment, the guide catheter 12 moves through the electrochemical process 130 at a rate of one foot per minute. The rate at which guide catheter 12 moves through process 130 also corresponds to the thickness of metallic substrate 102 plated on structural layer 16.

By varying the power supply to the electrochemical process 132 or the rate at which guide catheter 12 moves through electrochemical process 132, portions of guide catheter 12 structural layer 16 may be plated with varying degrees of thickness of metallic substrate 102. In one embodiment, the area forming the body of guide catheter 12 would include a metallic substrate 102 of greater thickness than the area of guide catheter 12 forming the tip.

It is recognized that other processes may be used which do not vary from the scope of this invention. For example, other metals may be plated onto guide catheter 12, different bath solutions may be used for the electrochemical process, or the strike bath may be eliminated while remaining within the scope of the present invention.

By forming a metallic substrate 102 on structural layer 16, a metallurgical connection forms between the braided strands 28 at a substantial number of points where they cross. The metallurgical connection provides increased tensile strength over less rigid non-metal connection, resulting in a more responsive guide catheter.

Figure 9:
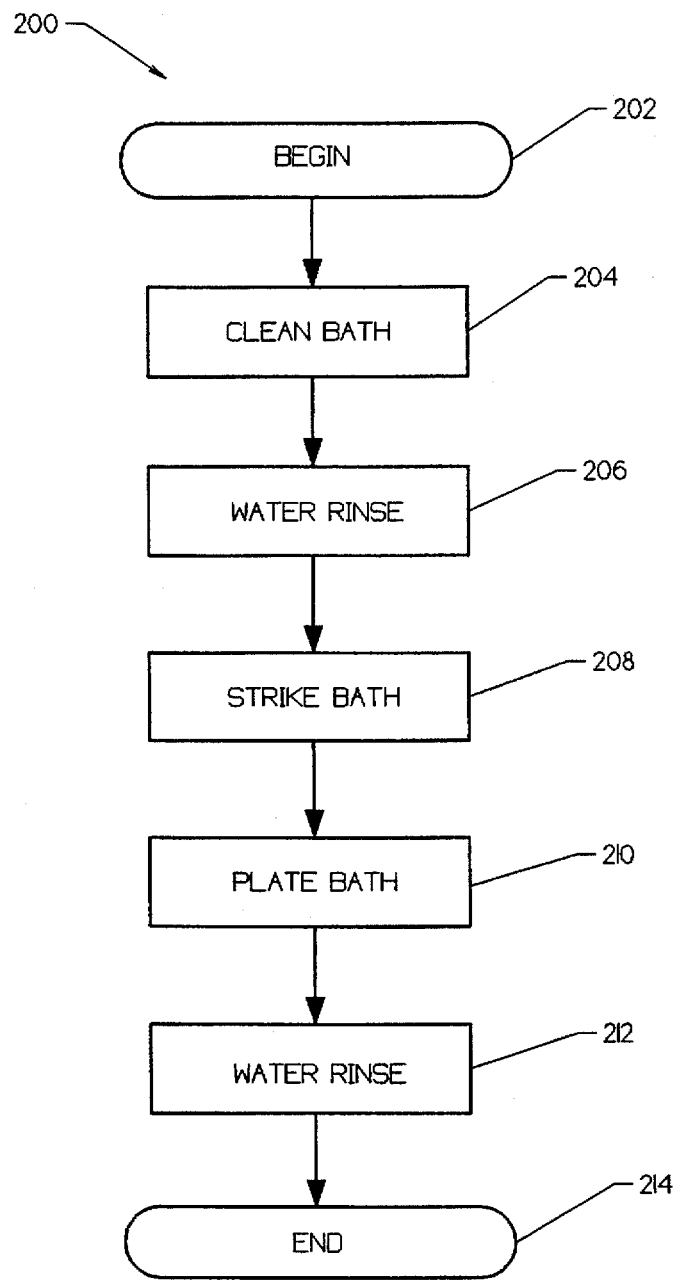
FIG. 9 is a flow diagram of the substrate process of FIG. 8.

Guide catheter 12 moves continuously through electrochemical process 130. FIG. 9 is a flow diagram of the electrochemical process 130 in FIG. 8, shown generally at 200. Electrochemical process 130 begins at 202. First, guide catheter 12 moves through clean bath 132 to prepare guide catheter 12 for plating a metallic substrate 102 over structural layer 16 (204). As guide catheter 12 moves through clean bath 132, clean bath 132 electrically scrubs and removes unwanted particles from the surface of structural layer 16.

Next, guide catheter 12 moves through water rinse 134 (206). Water rinse 134 rinses off the surface of guide catheter 12 for improving electrical conductivity of structural layer 16.

After passing through water rinse 134, guide catheter 12 moves through strike bath 136 (208). Strike bath 136 lays down a thin layer of metal, such as nickel, on structural layer 16. The thin layer of nickel provides for adherence of a greater mass of nickel in plate bath 138.

As guide catheter 12 moves through plate bath 138 (210), nickel is plated onto structural layer 16. The amount of nickel plated onto structural layer 16 is controlled by the power supplied from power supply C and the speed of guide catheter 12 moving through plate bath 138.

Lastly, guide catheter 12 receives a final rinsing as it moves through water rinse 140 (212). The electrochemical process 130 is now complete (214). Metallic substrate 102 attaches the structural layer 16 strands together at a substantial number of points where they cross, resulting in a highly responsive guide catheter 12.

It is recognized that the metal substrate may be applied to the structural layer by other methods to attach the braided strands together, such as passing an electrical current through the braided structural layer, spot welding or laser welding the braided strands, or by the use of other heating methods or chemical means. By attaching the braided strands together at a substantial number of points where they cross using a metal substrate, a more performance responsive catheter is formed due to a more rigid and secure structural layer 16.

It will be understood that this disclosure is, in many respects, only illustrative. Changes may be made in details, particularly in matters of shape, size, material, and arrangement of parts, without exceeding the scope of the invention. Accordingly, the scope of the invention is as defined in the language of the appended claims.

What is claimed is:

1. A unibody catheter, the catheter being used for percutaneous transluminal angioplasty procedures, the catheter including:
   a. a first layer; and
   b. a second layer coupled to the first layer, the second layer including a plurality of strands wherein the strands cross at a plurality of points, and further wherein the strands include means for fixedly attaching the strands to each other at a substantial number of the points where they cross.

2. The catheter of claim 1, wherein the strands include a core having a coating.

3. The catheter of claim 2, wherein the coating is a material different from the first layer.

4. The catheter of claim 2, wherein the coating is Nylon.

5. The catheter of claim 2, wherein the core is stainless steel wire.

6. The catheter of claim 2, wherein the core is nonmetallic.

7. The catheter of claim 1, wherein the fixing means include a metallic substrate over the strands.

8. The catheter of claim 7, wherein the metallic substrate is nickel.

9. The catheter of claim 7, wherein the metallic substrate is formed over the strands by an electrochemical process.

10. The catheter of claim 1 including a third layer formed over the second layer.

11. The catheter of claim 1, wherein the strands are braided.

12. The catheter of claim 1, wherein the second layer is at least partially embedded within the first layer.

13. The catheter of claim 1, wherein the strands are chemically attached together by said means for fixedly attaching the strands to each other.

14. The catheter of claim 1, wherein the strands are metallurgically attached together by said means for fixedly attaching the strands to each other.

15. A torque control guide catheter having a unibody, the unibody comprising:
   a. a tubular base member;
   b. a reinforcement member at least partially embedded in the tubular base member, the reinforcement member including a plurality of strands which cross at a plurality of points, the strands including means for fixedly attaching the strands together at a substantial number of points where they cross; and
   c. a cover layer formed over the tubular base member.

16. The catheter of claim 15, wherein the strands include a core having a coating.

17. The catheter of claim 16, wherein the coating is Nylon.

18. The catheter of claim 15, wherein the strands are braided.

19. The catheter of claim 15, wherein the strands are chemically bonded together by said means for fixedly attaching the strands to each other.

20. The catheter of claim 15, wherein the strands are metallurgically bonded together by said means for fixedly attaching the strands to each other.

21. The catheter of claim 15, wherein the fixing means includes a metallic substrate over the strands.

22. A unibody catheter comprising:
   a. a first layer;
   b. a second layer coupled to the first layer, the second layer including a plurality of strands wherein the strands cross at a plurality of points; and
   c. means carried by the strands for attaching the strands together at a substantial number of points where they cross.

23. The catheter of claim 22, wherein the means for attaching includes forming a substrate on the strands.

24. The catheter of claim 23, wherein the substrate is metallic.

25. The catheter of claim 24, wherein the metallic substrate includes nickel.

26. The catheter of claim 23, further including:
   means for selectively varying the amount of substrate formed on the strands.

27. The catheter of claim 22, wherein the means for attaching the strands together includes forming a substrate on the strands by an electrochemical process.

28. The catheter of claim 27, wherein the electrochemical process includes an electrolytic bath.

29. The catheter of claim 22, wherein the strands are metallurgically attached together.

30. A unibody catheter comprising:
   a first layer; and
   a second layer, the second layer including a plurality of strands which cross at a plurality of points;
   wherein the strands include a metallic core having a polymeric coating, and further wherein the polymeric coating attaches the strands together at a substantial number of points where they cross.

* * * * *